United States Patent
Ternansky et al.

(10) Patent No.: US 6,515,173 B1
(45) Date of Patent: Feb. 4, 2003

(54) INHIBITORS OF THE ICE/CED-3 FAMILY OF CYSTEINE PROTEASES

(75) Inventors: Robert J. Ternansky, Carlsbad, CA (US); Patricia L. Gladstone, San Diego, CA (US); Kevin J. Tomaselli, San Diego, CA (US)

(73) Assignee: Idun Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/482,813

(22) Filed: Jan. 13, 2000

(51) Int. Cl.$^7$ .................................. C07K 5/06
(52) U.S. Cl. .................. 562/553; 514/19; 562/563; 562/576
(58) Field of Search ............... 514/19; 562/571, 562/553, 563, 576; 530/300

(56) References Cited

U.S. PATENT DOCUMENTS

| | | | |
|---|---|---|---|
| 5,869,519 A | 2/1999 | Karanewsky et al. | 514/415 |
| 5,877,197 A | 3/1999 | Karanewsky et al. | 514/397 |
| 5,968,927 A | 10/1999 | Karanewsky et al. | 514/214 |

FOREIGN PATENT DOCUMENTS

| | | |
|---|---|---|
| EP | 618 223 A2 | 10/1994 |
| EP | 623 592 A1 | 11/1994 |
| GB | 2 292 149 A | 2/1996 |
| WO | WO 97/22619 | 6/1997 |
| WO | WO 00/01666 | 1/2000 |

OTHER PUBLICATIONS

Gagliardini et al., "Prevention of Vertebrate Neuronal Death by the crmA Gene," *Science* 263:826–828, 1994.

Marx, "Cell Death Studies Yield Cancer Clues," *Science* 259:760–761, 1993.

Okamoto et al., "Peptide Based Interleukin–1β Converting Enzyme (ICE) Inhibitors: Synthesis, Structure Activity Relationships and Crystallographic Study of the ICE–inhibitor Complex," *Chem. Pharm. Bull.* 47(1):11–21, 1999.

Sleath et al., "Substrate Specificity of the Protease That Processes Human Interleukin–1β," *The Journal of Biological Chemistry* 265(24):14526–14528, 1990.

Patent Abstracts of Japan, Abstract of JP 11–147873, vol. 1999, No. 11, Sep. 30, 1999.

*Primary Examiner*—David Lukton
(74) *Attorney, Agent, or Firm*—Seed Intellectual Property Law Group PLLC

(57) ABSTRACT

This invention s directed to novel oxamyl dipeptide ICE/ced-3 family inhibitor compounds having the following structure:

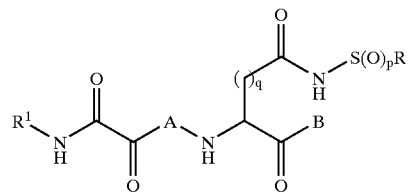

wherein A, B, R, $R_1$, p and q are as defined herein. The invention s all directed to pharmaceutical compositions containing one or more of thee compound, as well as to the use of such compositions in the treatment of patients suffering inflammatory, autoimmune and neurodegenerative diseases, for the prevention of ischemic injury, and for the preservation of organs that to undergo a transplantation procedure.

24 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Substrate for the ICE assay.

<400> SEQUENCE: 1

Tyr Val Ala Asp
 1

<210> SEQ ID NO 2
<211> LENGTH: 4
<212> TYPE: PRT
<213> ORGANISM: Artificial Sequence
<220> FEATURE:
<223> OTHER INFORMATION: Substrate for the CPP32, Mch2, Mch3 and Mch5
      assays.

<400> SEQUENCE: 2

Asp Glu Val Asp
 1

INHIBITORS OF THE ICE/CED-3 FAMILY OF CYSTEINE PROTEASES

TECHNICAL FIELD

The present invention relates to novel classes of compounds which are inhibitors of interleukin-1β converting enzyme and related proteases ("ICE/ced-3 family of cysteine proteases"), as well as pharmaceutical compositions comprising these compounds and to methods of using such pharmaceutical compositions.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today*, 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.*, 84:4572–4576 (1987); Lonnemann, G. et al., *Eur. J. Immunol.*, 19:1531–1536 (1989).

IL-1β is synthesized as a biologically inactive precursor, proIL-1β. ProIL-1β is cleaved by a cysteine protease called interleukin-1β converting enzyme ("ICE") between Asp-116 and Ala-117 to produce the biologically active C-terminal fragment found in human serum and synovial fluid. Sleath, P. R. et al., *J. Biol. Chem.*, 265:14526–14528 (1992); A. D. Howard et al., *J. Immunol.*, 147:2964–2969(1991).

ICE is a cysteine protease localized primarily in monocytes. In addition to promoting the pro-inflammatory and immunoregulatory properties of IL-1β, ICE, and particularly its homologues, also appear to be involved in the regulation of cell death or apoptosis. Yuan, J. et al., *Cell*, 75:641–652 (1993); Miura, M. et al., *Cell*, 75:653–660 (1993); Nett-Giordalisi, M. A. et al., *J. Cell Biochem.*, 17B:117 (1993). In particular, ICE or ICE/ced-3 homologues are thought to be associated with the regulation of apoptosis in neurogenerative diseases, such as Alzheimer's and Parkinson's disease. Marx, J. and M. Baringa, *Science*, 259:760–762 (1993); Gagliardini, V. et al., *Science*, 263:826–828 (1994).

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases, such as Alzheimer's and Parkinson's disease. Such inhibitors are also useful for the repopulation of hematopoietic cells following chemo- and radiation therapy and for prolonging organ viability for use in transplantation.

ICE/ced-3 inhibitors represent a class of compounds useful for the control of the above-listed disease states. Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. These undesirable properties have hampered their development into effective drugs.

Accordingly, the need exists for compounds that can effectively inhibit the action of the ICE/ced-3 family of proteases, for use as agents for preventing unwanted apoptosis, and for treating chronic and acute forms of IL-1 mediated diseases such as inflammatory, autoimmune or neurodegenerative diseases. The present invention satisfies this need and provides further related advantages.

SUMMARY OF THE INVENTION

In general, the compounds of this invention incorporate a sulfonamido ($NHSO_2$) or sulfinamido (NHSO) modified (N-substituted)oxamyl group as a dipeptide mimetic. The resulting compounds exhibit improved properties relative to their peptidic counterparts, for example, such as improved cell penetration or improved absorption and metabolic stability resulting in enhanced bioavailability.

One aspect of the instant invention is the compounds of the following Formula I:

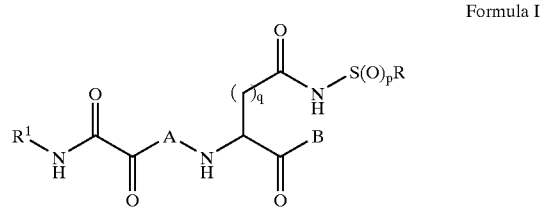

Formula I wherein A, B, R, $R^1$, p and q are as defined below, as well as pharmaceutically acceptable salts thereof.

A further aspect of the instant invention is a pharmaceutical composition comprising a compound of the above Formula I and a pharmaceutically-acceptable carrier therefor.

Another aspect of this invention involves a method for treating an autoimmune disease comprising administering an effective amount of a pharmaceutical composition discussed above to a patient in need of such treatment.

Yet another aspect of the instant invention is a method for treating an inflammatory disease comprising administering an effective amount of a pharmaceutical composition discussed above to a patient in need of such treatment.

A further aspect of the instant invention is a method for treating a neurodegenerative disease comprising administering an effective amount of a pharmaceutical composition discussed above to a patient in need of such treatment.

Another aspect of the instant invention is a method of preventing ischemic injury to a patient suffering from a disease associated with ischemic injury comprising administering an effective amount of the pharmaceutical composition discussed above to a patient in need of such treatment.

A further aspect of the instant invention is a method for expanding of hematopoietic cell populations and/or enhancing their survival by contacting the cells with an effective amount of the pharmaceutical composition discussed above. Cell populations included in the method of the invention include (but are not limited to) granulocytes, monocytes, erthrocytes, lymphocytes and platelets for use in cell transfusions.

An alternate aspect of the instant invention is a method of prolonging the viability of an organ that has been removed from the donor for the purpose of a future transplantation procedure, which comprises applying an effective amount of the pharmaceutical composition discussed above to the organ, thereby prolonging the viability of the organ as compared to an untreated organ. The organ may be an intact organ, or isolated cells derived from an organ (e.g., isolated pancreatic islet cells, isolated dopaminergic neurons, blood or hematopoietic cells).

These and other aspects of this invention will be evident upon reference to the following detailed description.

DETAILED DESCRIPTION OF THE INVENTION

As mentioned above, one aspect of the instant invention is the compounds of the Formula I:

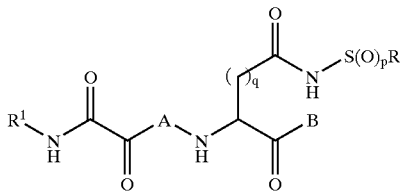

Formula I wherein:

p is 1 or 2;

q is 1 or 2;

R and $R^1$ are the same or different and independently alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, substituted (heteroaryl)alkyl, $R^{1a}(R^{1b})N$ or $R^{1c}O$;

A is a natural or unnatural amino acid of Formula IIa–i:

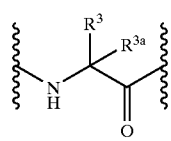

IIa

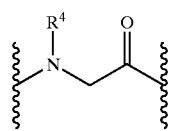

IIb

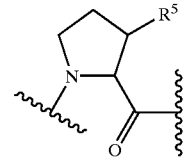

IIc

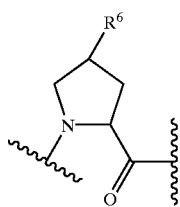

IId

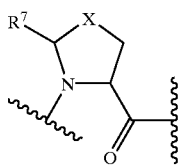

IIe

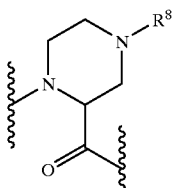

IIf

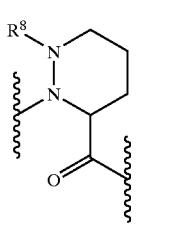

IIg

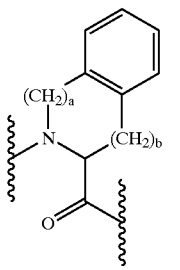

IIh

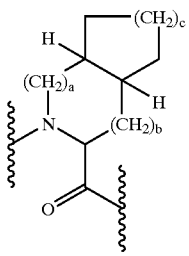

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, $(CH_2)_n$cycloalkyl, $(CH_2)_n$phenyl, $(CH_2)_n$(substituted phenyl), $(CH_2)_n$(1 or 2-naphthyl), $(CH_2)_n$(substituted 1 or 2-naphthyl), $(CH_2)_n$(heteroaryl), $(CH_2)_n$(substituted heteroaryl), halomethyl, $CO_2R^{12}$, $CONR^{13}R^{14}$, $CH_2ZR^{15}$, $CH_2OCO(aryl)$, $CH_2OCO$(heteroaryl), or $CH_2OPO(R^{16})R^{17}$, where Z is an oxygen or a sulfur atom, or B is a group of the Formula IIIa–c:

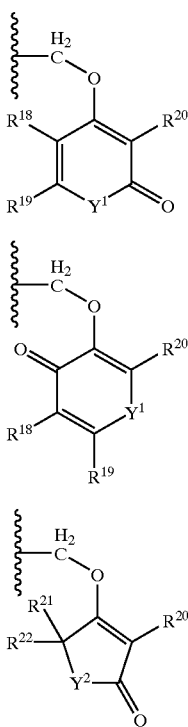

and wherein:
- $R^{1a}$ and $R^{1b}$ are the same or different and, at each occurrence, independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl, with the proviso that $R^{1a}$ and $R^{1b}$ cannot both be hydrogen;
- $R^{1c}$ is, at each occurrrence, alkyl, cycloalkyl, (cycloalkyl) alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl;
- $R^3$ is $C_{1-6}$ lower alkyl, cycloalkyl, phenyl, substituted phenyl, $(CH_2)_nNH2$, $(CH_2)_nNHCOR^9$, $(CH_2)_nN(C=NH)NH_2$, $(CH_2)_mCO_2R^2$, $(CH_2)_mOR^{10}$, $(CH_2)_mSR^{11}$, $(CH_2)_n$cycloalkyl, $(CH_2)_n$phenyl, $(CH_2)_n$(substituted phenyl), $(CH_2)_n$(1 or 2-naphthyl) or $(CH_2)_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;
- $R^{3a}$ is hydrogen or methyl, or $R^3$ and $R^{3a}$ taken together are $-(CH_2)_d-$ where d is an interger from 2 to 6;
- $R^4$ is phenyl, substituted phenyl, $(CH_2)_m$phenyl, $(CH_2)_m$(substituted phenyl), cycloalkyl, or benzofused cycloalkyl;
- $R^5$ is hydrogen, lower alkyl, cycloalkyl, plienyl, substituted phenyl, $(CH_2)_n$cycloalkyl, $(CH_2)_n$phenyl, $(CH_2)_n$(substituted phenyl), or $(CH_2)_n$(1 or 2-naphthyl);
- $R^6$ is hydrogen, fluorine, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, $SR^{11}$ or $NHCOR^9$;
- $R^7$ is hydrogen, oxo (i.e., =O), lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);
- $R^8$ is lower alkyl, cycloalkyl, $(CH_2)_n$cycloalkyl, $(CH_2)_n$phenyl, $(CH_2)_n$(substituted phenyl), $(CH_2)_n$(1 or 2-naphthyl), or $COR^9$;
- $R^9$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{12}$, or $NR^{13}R^{14}$;
- $R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);
- $R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);
- $R^{12}$ is lower alkyl, cycloalkyl, $(CH_2)_n$cycloalkyl, $(CH_2)_n$phenyl, $(CH_2)_n$(substituted phenyl), or $(CH_2)_n$(1 or 2-naphthyl);
- $R^{13}$ is hydrogen, lower alkyl, cycloalkyl, phenyl, substituted phenyl, naphthyl, substituted naphthyl, $(CH_2)_n$cycloalkyl, $(CH_2)_n$phenyl, $(CH_2)_n$(substituted phenyl), or $(CH_2)_n$(1 or 2-naphthyl);
- $R^{14}$ is hydrogen or lower alkyl;
- or $R^{13}$ and $R^{14}$ taken together form a five to seven membered carbocyclic or heterocyclic ring, such as morpholine, or N-substituted piperazine;
- $R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);
- $R^{16}$ and $R^{17}$ are independently lower alkyl, cycloalkyl, phenyl, substituted phenyl, naphthyl, phenylalkyl, substituted phenylalkyl, or (cycloalkyl)alkyl;
- $R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are $-(CH=CH)_2-$;
- $R^{20}$ is hydrogen, alkyl, phenyl, substituted phenyl, $(CH_2)_n$phenyl, $(CH_2)_n$(substituted phenyl);
- $R^{21}$, $R^{22}$ and $R^{23}$ are independently hydrogen, or alkyl;
- X is $CH_2$, $(CH_2)_2$, $(CH_2)_3$, or S;
- $Y^1$ is O or $NR^{23}$;
- $Y^2$ is $CH_2$, O, or $NR^{23}$;
- a is 0 or 1 and b is 1 or 2, provided that when a is 1 then b is 1;
- c is 1 or 2, provided that when c is 1 then a is 0 and b is 1;
- m is 1 or 2; and
- n is 1, 2, 3 or 4;
- or a pharmaceutically acceptable salt thereof.

As used herein, the term "alkyl" means a straight or branched $C_1$ to $C_{10}$ carbon chain, such as methyl, ethyl, tert-butyl, iso-propyl, n-octyl, and the like. The term "lower alkyl" means a straight chain or branched $C_1$ to $C_6$ carbon chain, such as methyl, ethyl, iso-propyl, and the like.

The term "cycloalkyl" means a mono-, bi-, or tricyclic ring that is either fully saturated or partially unsaturated. Examples of such a ring include cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted with one of the above cycloalkyl rings. Examples of such a group include (cyclohexyl) methyl, 3-(cyclopropyl)-n-propyl, 5-(cyclopentyl)hexyl, 6-(adamantyl)hexyl, and the like.

The term "substituted phenyl" specifies a phenyl group substituted with one or more substituents chosen from halogen, hydroxy, protected hydroxy, cyano, nitro, trifluoromethyl, alkyl, alkoxy, acyl, acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-(lower alkyl) carboxamide, protected N-(lower alkyl)carboxamide, N,N-di(lower alkyl)carboxamide, N-((lower alkyl)sulfonyl) amino, N-(phenylsulfonyl)amino or by a substituted or unsubstituted phenyl group, such that in the latter case a biphenyl or naphthyl group results, or wherein two adjacent alkyl substituents on the substituted phenyl ring taken together form a cycloalkyl to yield, for example, tetrahydronaphthyl or indanyl.

Examples of the term "substituted phenyl" includes a mono-, di-, tri-, tetra- or penta(halo)phenyl group such as 2-, 3- or 4-chlorophenyl, 2,6-dichlorophenyl, 2,5-dichlorophenyl, 3,4-dichlorophenyl, 2-,3- or 4-bromophenyl, 3,4-dibromophenyl, 3-chloro-4-fluorophenyl, 2-, 3- or 4-fluorophenyl, 2,4,6-trifluorophenyl, 2,3,5,6-tetrafluorophenyl, 2,3,4,5-tetrafluorophenyl, 2,3,4,5,6-pentafluorophenyl, and the like; a mono or di(hydroxy) phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-,3- or 4-cyanophenyl; a mono- or di(alkyl)phenyl group such as 2-, 3-, or 4-methylphenyl, 2,4-dimethylphenyl, 2-, 3- or 4-(isopropyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy)phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "phenylalkyl" means one of the above phenyl groups attached to one of the above-described alkyl groups, and the term "substituted phenylalkyl" means that either the phenyl or the alkyl, or both, are substituted with one or more of the above-defined substituents. Examples of such groups include 2-phenyl-1-chloroethyl, 2-(4'-methoxyphenyl)ethyl, 4-(2', 6'-dihydroxy phenyl)n-hexyl, 2-(5'-cyano-3'-methoxyphenyl)n-pentyl, 3-(2', 6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl, and the like.

The term "substituted naphthyl" means a naphthyl group sustituted with one or more of the above-identified subtituents, and the term "(1 or 2 naphthyl)alkyl" means a naphthyl (1 or 2) attached to one of the above-described alkyl groups.

The terms "halo" and "halogen" refer to the fluoro, chloro, bromo or iodo groups. These terms may also be used to describe one or more halogens, which are the same or different. Preferred halogens in the context of this invention are chloro and fluoro.

The term "aryl" refers to aromatic five and six membered carbocyclic rings. Six membered rings are preferred.

The term "heteroaryl" denotes optionally substituted aromatic five-membered or six-membered heterocyclic rings that have 1 to 4 heteroatoms, such as oxygen, sulfur and/or nitrogen atoms, in particular nitrogen, either alone or in conjunction with sulfur or oxygen ring atoms.

The following ring systems are representative examples of the heterocyclic radicals denoted by the term "heteroaryl" (whether substituted or unsubstituted): thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups.

Substituents for the heteroaryl group are as defined above, or as set forth below. As used in conjunction with the above substituents for heteroaryl rings, "trihalomethyl" can be trifluoromethyl, trichloromethyl, tribromomethyl or triiodomethyl, "lower alkoxy" means a $C_1$ to $C_4$ alkoxy group, similarly, "lower alkylthio" means a $C_1$ to $C_4$ alkylthio group. The term "substituted lower alkyl" means the above-defined lower alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt.

As used in conjunction with the substituents for the heteroaryl rings, the terms "substituted (cycloalkyl)alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different. The term "heteroaryl(alkyl)" denotes an alkyl group as defined above, substituted at any position by a heteroaryl group, as above defined.

Furthermore, the above optionally substituted five-membered or six-membered heterocyclic rings, and the above cycloalky rings, can optionally be fused to a aromatic 5-membered or 6-membered aryl or heteroaryl ring system. For example, the rings can be optionally fused to an aromatic 5-membered or 6-membered ring system such as a pyridine or a triazole system, and preferably to a benzene ring.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); and ammonium ion; and the organic cations (for example, dibenzylammonium, benzylammonium, 2-hydroxyethylammonium, bis(2-hydroxyethyl)ammonium, phenylethylbenzyl-ammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyidimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl (THP), 2-methoxyprop-2-yl, 1-ethoxyeth-1-yl, methoxymethyl, βmethoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C.B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tetrahydropyranyl (THP) group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl ("Ddz"), 2-(p-toluyl)propyl-2-oxycarbonyl, cyclopentanyloxycarbonyl, 1-methylcyclopentanyl-oxycarbonyl, cyclohexanyloxycarbonyl, 1-methyl-cyclohexanyloxy-carbonyl, 2-methylcyclohexanyl-oxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenyl-methoxycarbonyl ("Fmoc"), 2-(trimethylsilyl) ethoxycarbonyl, allyloxycarbonyl, 1-(trimethylsi lylmethyl) prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobomyloxycarbonyl, 1-piperidyloxycarbonyl, benzyl-oxycarbonyl ("Cbz"), 4-phenylbenzyloxycarbonyl, 2-methylbenzyloxycarbonyl, α-2,4,5,-tetramethylbenzyl-oxycarbonyl ("Tmz"), 4-methoxybenzyloxycarbonyl, 4-fluorobenzyl-oxycarbonyl, 4-chlorobenzyloxycarbonyl, 3-chlorobenzyloxycarbonyl, 2-chlorobenzyloxy-carbonyl, 2,4-dichlorobenzyloxycarbonyl, 4-bromobenzyloxycarbonyl, 3-bromobenzyloxy-carbonyl, 4-nitrobenzyloxycarbonyl, 4-cyanobenzyloxycarbonyl, 4-(decyloxy)benzyloxy-carbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenylsulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New York, N.Y., 1984 and 1993, and J. M. Stewart and J. D. Young, "Solid Phase Peptide Synthesis," 2nd Ed., Pierce Chemical Co., Rockford, Ill, 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acid" refers to both the naturally occurring amino acids and other non-proteinogenic cc-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, y-carboxyglutamic acid, arginine, ornithine and lysine. Examples of unnatural alpha-amino acids include hydroxylysine, citrulline, kynurenine, (4-aminophenyl) alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxy-kynurenine, 3-aminotyrosine, trifluoromethylalanine, 2-thienylalanine, (2-(4-pyridyl) ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydro-proline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β2- and 3-thienylalanine; β2- and 3-furanylalanine; β2-, 3- and 4-pyridylalanine; β-(benzothienyl-2- and 3-yl)alanine; β-(1- and 2-naphthyl) alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine. Any of these α-amino acids may be substituted with a methyl group at the alpha position, a halogen at any position of the aromatic residue on the α-amino side chain, or an appropriate protective group at the O, N, or S atoms of the side chain residues. Appropriate protective groups are discussed above.

The compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the group donated as "A" in Formula I or the modified aspartic acid residue attached to the group denoted as "A".

With regard to the p and q groups of Forumula I, typical embodiments include compounds wherein q is 1 and p is 2.

Compounds of this invention with respect to the R and $R^1$ groups in Formula I, include those wherein:
R is lower alkyl; and
$R^1$ is phenyl, substituted phenyl, phenylalkyl, substituted phenylalkyl, naphthyl, substituted naphthyl, (1 or 2 naphthyl)alkyl, heteroaryl, or (heteroaryl)alkyl.

More typically, the compounds of this invention with respect to the R and $R^1$ groups include those wherein:
R is methyl; and
$R^1$ is phenyl, substituted phenyl, phenylalkyl, substituted phenylalkyl, naphthyl, substituted naphthyl, or (1 or 2 naphthyl)alkyl.

Compounds of this invention with respect to the A group in Formula I, include those of Formula IIa wherein:
$R^3$ is lower alkyl, cycloalkyl, phenyl, substituted phenyl, $(CH_2)_nNH_2$, $(CH_2)_mOR^{10}$, $(CH_2)_mSR^{11}$, $(CH_2)_n$cycloalkyl, $(CH_2)_n$phenyl, $(CH_2)_n$(substituted phenyl), or $(CH_2)_n$(1 or 2-naphthyl);
$R^{3a}$ is hydrogen;
$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);
$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl); and
n=1–4 and m=1 or 2.

Compounds of this invention with respect to the A group in Formula I also include those of Formula IIb wherein:
$R^4$ is phenyl, substituted phenyl, $(CH_2)_m$phenyl, $(CH_2)_n$(substituted phenyl), cycloalkyl, or 2-indanyl; and
m=1 or 2.

Another group of compounds with respect to the A group in Formula I include those of Formula IId wherein:
$R^6$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$;
$R^{10}$ and $R^{11}$ are independently cycloalkyl, phenyl, substituted phenyl, naplithyl, $(CH_2)_n$cycloalkyl, $(CH_2)_n$phenyl, $(CH_2)_n$(substituted phenyl), or $(CH_2)_n$(1 or 2-naphthyl); and
n=1–4.

A fourth group of compounds with respect to the A group in Formula I include those of Formula IIe wherein:

$R^7$ is hydrogen, oxo, cycloalkyl, phenyl, substituted phenyl, or naphthyl; and $X=CH_2$, $(CH_2)_2$, $(CH_2)_3$, or S.

Another group of compounds with respect to the A group in Formula I include those of Formula IIh wherein:

a=0 and b=1 or 2.

Compounds of this invention with respect to the B group in Formula I include those wherein:

B is hydrogen, 2-benzoxazolyl, substituted 2-oxazolyl, $CH_2ZR^{15}$, $CH_2OCO(aryl)$, or $CH_2OPO(R^{16})R^{17}$, where Z is an oxygen or a sulfur atom;

$R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl); and $R^{16}$ and $R^{17}$ are independently alkyl, cycloalkyl, phenyl, substituted phenyl, naphthyl, phenylalkyl, substituted phenylalkyl, or (cycloalkyl)alkyl.

Another group of compounds with respect to the B group in Formula I include those of Formula IIIa–c wherein:

$Y^1$ is O or $NR^{23}$;

$Y^2$ is $CH_2$, O, or $NR^{23}$;

$R^{18}$ and $R^{19}$ are independently hydrogen, alkyl, or phenyl, or $R^{18}$ and $R^{19}$ taken together are $—(CH=CH)_2—$;

$R^{20}$ is hydrogen, alkyl, phenyl, substituted phenyl, $(CH_2)_n$phenyl, or $(CH_2)_n$(substituted phenyl); and $R^{21}$, $R^{22}$ and $R^{23}$ are independently hydrogen or alkyl.

The compounds of Formula I may be synthesized using conventional techniques, as well as by the following Reaction Scheme. To that end, in the following Reaction Scheme, q is 1, and corresponding compounds wherein q is 2 may be made in the same manner by employing the corresponding ethylene ($—CH_2CH_2—$) starting material in place of the methylene ($—CH_2—$) moiety.

Reaction Scheme

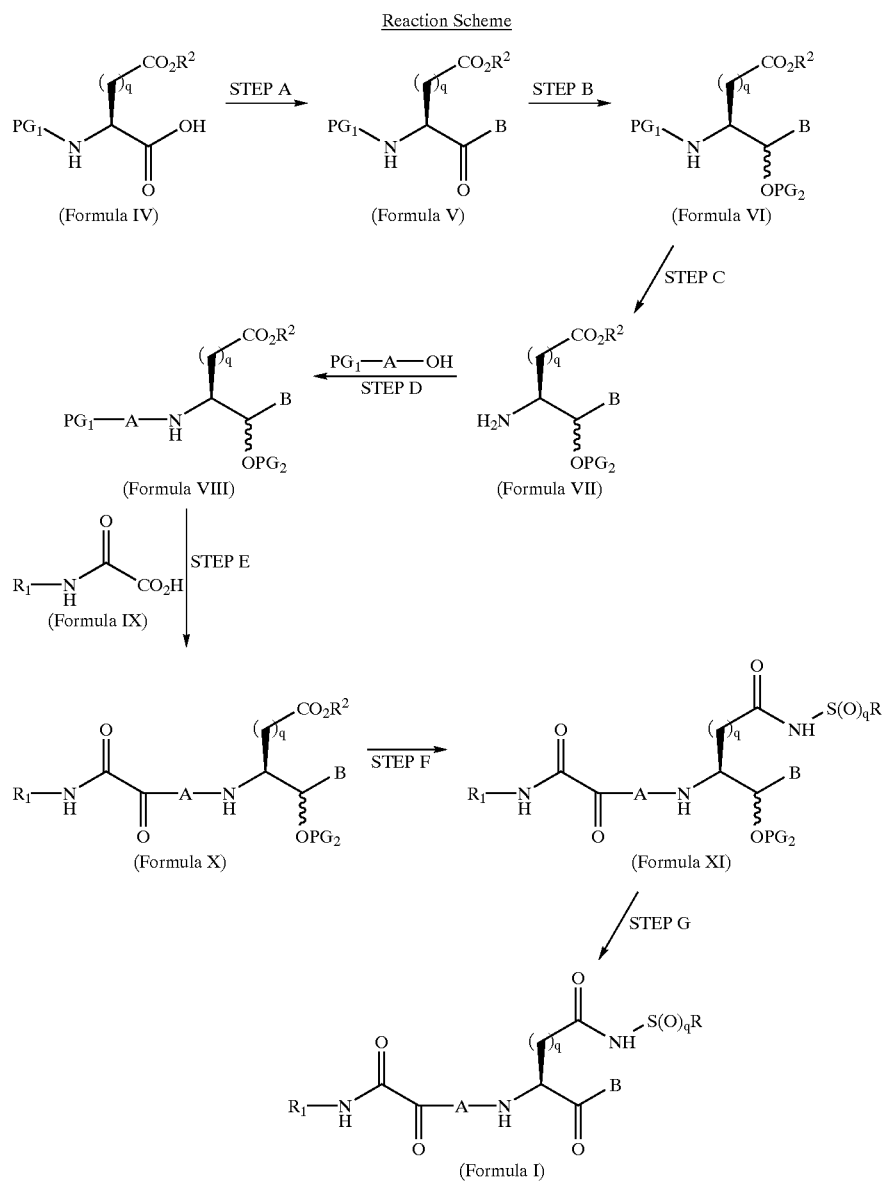

In the above Scheme 1, $R^2$ represents hydrogen or a carboxy protecting group, wherein the carboxy protecting group is as defined above. "$PG_1$" stands for an amino protecting group, "$PG_2$" stands for a hydroxy-protecting group, and "A" stands for a natural or unnatural amino acid of formula IIa through IIi, as discussed above.

The modified aspartic acids of Formula V can be prepared by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference. For example, in Step A, the carboxylic acid moiety of Formula IV is converted to its bromomethyl ketone which is then treated with either $R^{15}Z$—H, (aryl)—$CO_2H$, (heteroaryl)—$CO_2H$, or $R^{16}(R^{17})PO_2H$ in the presence of an inorganic base such as potassium carbonate or potassium fluoride in an inert solvent such as dimethyl formamide to give the corresponding intermediate of Formula V in which B is $CH_2ZR^{15}$, $CH_2OCO(aryl)$, $CH_2OCO$(heteroaryl), or $CH_2OPO(R^{16})R^{17}$, respectively.

Reduction of the carbonyl group in Formula V (Step B) with a hydride reducing agent such as sodium borohydride gives rise to a diastereomeric mixture of alcohols which are further protected with a hydroxy-protecting group ($PG_2$) as referenced above.

The coupling reaction carried out under Step D is performed in the presence of a standard peptide coupling agent such as the combination of the combination of dicyclohexylcarbodiimide(DCC) and 1-hydroxybenzotriazole(HOBt), as well as the BOP (benzotriazolyloxy-tris-(dimethylamino)phosphonium hexafluorophosphate) reagent, pyBOP (benzotriazolyloxy-tris(N-pyrolidinyl)phosphoniumhexafluorophosphate), HATU (O-7-Azabenzotriazol-1-yl-tetramethylisouronium-hexafluorophosphate), HBTU (O-benzotriazolyly-tetramethylisouronium-hexafluorophosphate), and EEDQ (1-ethyloxycarbonyl-2-ethyloxy-1,2-dihydroquinoline) reagents, the combination of 1-ethyl(3,3'-dimethyl-1'-aminopropyl)carbodiimide (EDAC) and HOBt, and the like, as discussed in J. Jones, "Amino Acid and Peptide Synthesis," Steven G. Davis ed., Oxford University Press, Oxford, pp. 25–41(1992); M. Bodanzky, "Principles of Peptide Synthesis," Hafner et al. ed., Springer-Verlag, Berlin Heidelberg, pp. 9–52 and pp. 202–251 (1984); M. Bodanzky, "Peptide Chemistry, A Practical Textbook," Springer-Verlag, Berlin Heidelberg, pp. 55–73 and pp. 129–180; and Stewart and Young, "Solid Phase Peptide Synthesis," Pierce Chemical Company, (1984), all of which are herein incorporated by reference. The amino protecting group is then removed and the resulting amine is coupled to the (N-substituted) oxamic acid of Formula IX (Step E). Again, this coupling reaction uses the standard peptide coupling reactions mentioned above.

Conversion of the carboxylate of Formula X to the sulfonimide (Step F) involves removal of the carboxy protecting group ($R_2$) using standard conditions well known in the art. The resulting carboxylic acid is then treated with CDI (2 eq.) in THF at room temperature for 3 hours, followed by $H_2NS(O)_qR$ (2 eq.) in DBU (2 eq.) at room temperature for 4 hours.

The sulfonimide intermediate of Formula XI is reacted in Step G with TsOH (0.4 eq.) in methanol at room temperature for 30 minutes to de-protect the alcohol, which may be converted to the corresponding carbonyl of Formula I by employing the Dess-Martin periodinane reagent and DCM at room temperature for 30 minutes.

Pharmaceutical compositions of this invention comprise any of the compounds of the present invention, and pharmaceutically acceptable salts thereof, with any pharmaceutically acceptable carrier, adjuvant or vehicle (hereinafter collectively referred to as "pharmaceutically-acceptable carriers"). Pharmaceutically acceptable carriers, adjuvants and vehicles that may be used in the pharmaceutical compositions of this invention include, but are not limited to, ion exchange, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

The pharmaceutical compositions of this invention may be administered orally, parenterally, by inhalation spray, topically, rectally, nasally, buccally, vaginally or by an implanted reservoir. Oral and parenteral administration are preferred. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyidithiocarbamate, tumor necrosis factor, naltrexons and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical compositions according to this invention may be comprised of a combination of a compound of Formula I and another therapeutic or prophylactic agent mentioned above.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). As a consequence of their ability to inhibit apoptosis, the present pharmaceutical compositions are also useful for the repopulation of hematopoietic cells of a patient following chemotherapy. Methods of administering an effective amount of the above-described pharmaceutical compositions to mammals, also referred to herein as patients, in need of such treatment (that is, those suffering from inflammatory diseases, autoimmune diseases, neurodegenerative diseases and for the repopulation of hematopoietic cells in cancer patients who have undergone chemotherapy) are another aspect of the instant invention. Finally, as a further consequence of their ability to inhibit apoptosis, the instant pharmaceutical compositions may be used in a method to prolong the viability of organs to be used in transplantations.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative diseases include, for example, amyotrophic lateral sclerosis, Alzheimer's disease, Parkinson's disease, and primary lateral sclerosis. The pharmaceutical compositions of this invention may also be used to promote wound healing. Target diseases associated with harmful, apoptosis, in other words, those associated with ischemic injury, includes myocardial infarction, stroke, and ischemic kidney disease. The pharmaceutical compositions of this invention may also be used to treat infectious diseases, especially those involved with viral infections.

The term "effective amount" refers to dosage levels of the order of from about 0.05 milligrams to about 140 milligrams per kilogram of body weight per day for use in the treatment of the above-indicated conditions (typically about 2.5 milligrams to about 7 grams per patient per day). For example, inflammation may be effectively treated by the administration of from about 0.01 to 50 milligrams of the compound per kilogram of body weight per day (about 0.5 milligrams to about 3.5 grams per patient per day).

The amount of the compounds of Formula I that may be combined with the carrier materials to produce a single dosage form will vary depending upon the host treated and the particular mode of administration. For example, a formulation intended for the oral administration of humans may contain from 0.5 milligrams to 5 grams of a compound of Formula I combined with an appropriate and convenient amount of a pharmaceutically-acceptable carrier which may vary from about 5 to about 95 percent of the total composition. Dosage unit forms will generally contain between from about 1 milligram to about 500 milligrams of an active compound of Formula I.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing prevention or therapy.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cystine protease inhibitors will be evident to those of ordinary skill in the art.

In order that this invention be more fully understood, the following examples are set forth. These examples are for the purpose of illustration only and are not to be construed as limiting the scope of the invention in any way.

In the following Examples, proton NMR spectra were obtained at 300 MHz; chemical shifts are quoted downfield from internal tetramethylsilane.

EXAMPLE 1

Assay for Inhibition of ICE/ced-3 Protease Family Activity

A. Determination of $IC_{50}$ Values

Fluorescence enzyme assays detecting the activity of the compounds of Formula I utilizing the recombinant ICE and CPP32 enzymes are performed essentially according to Thorrberry et al. (*Nature*, 356:768:774 (1992)) and Nicholson et al. (*Nature*, 376:37–43 (1995)) respectively, (herein incorporated by reference) in 96 well microtiter plates. The substrate is Acetyl-Tyr-Val-Ala-Asp-amino-4-methylcoumarin (AMC) (SEQ ID NO: 1) for the ICE assay and Acetyl-Asp-Glu-Val-Asp-amino-4-methylcoumarin (SEQ ID NO: 2) for the CPP32, Mch2, Mch3 and Mch5 assays. Enzyme reactions are run in ICE buffer (25 mM HEPES, 1 mM EDTA, 0.1% CHAPS, 10% sucrose, pH 7.5) containing 2 mM DTT at room temperature in duplicate. The assays are performed by mixing the following components:

50 μL ICE, Mch2, Mch5, CPP32 (18.8, 38, 8.1 and 0.153 nM concentrations, respectively) or Mch3 (1 unit) enzyme in ICE buffer containing either 8.0 (ICE, Mch2, Mch3, CPP32) or 20 (Mch5) mM DTT;

50 μL compound of Formula I or ICE buffer (control); and

100 μL of 20 IM substrate.

The enzyme and the compound of Formula I to be assayed are allowed to preincubate in the microtitre plate wells for 30 minutes at room temperature prior to the addition of substrate to initiate the reaction. Fluorescent AMC product formation is monitored for one hour at room temperature by measuring the fluorescence emission at 460 nm using an excitation wavelength of 360 nm. The fluorescence change in duplicate (control) wells are averaged and the mean values are plotted as a function of inhibitor concentration to determine the inhibitor concentration producing 50% inhibition ($IC_{50}$).

B. Determination of the Dissociation Constant Ki and Irreversible Rate Constant $k_3$ for Irreversible Inhibitors For the irreversible inhibition of a ICE/ced-3 Family Protease enzyme with a competitive irreversible inhibitor; using the model represented by the following formulas:

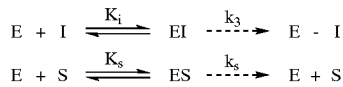

The product formation at time t may be expressed as:

$$[P]_t = [E]^T\left(\frac{[S]K_i}{[I]K_s}\right)\left(\frac{k_s}{k_3}\right)\left[1 - e^{-k_3 t/\left(1+\frac{K_i}{[I]}\left(1+\frac{[S]}{K_s}\right)\right)}\right] \quad \text{Equation 3}$$

where E, I, EI and E-I denote the active enzyme, inhibitor, non-covalent enzyme-inhibitor complex and covalent enzyme-inhibitor adduct, respectively. The $K_i$ value is the overall dissociation constant of the reversible binding steps, and $k_3$ is the irreversible rate constant. The [S] and $K_s$ values are the substate concentration and dissociation constant of the substrate bound to the enzyme, respectively. $[E]^T$ is the total enzyme concentration.

EXAMPLE 2

3S)-N-Methanesulfonyl-3-[N-(N'-(2-t-Butylphenyl) Oxamyl)Valinyl] Amino-5-(2',3',5',6'-Tetrafluorophenoxy)-4-Oxapentanamide Compound No. 1

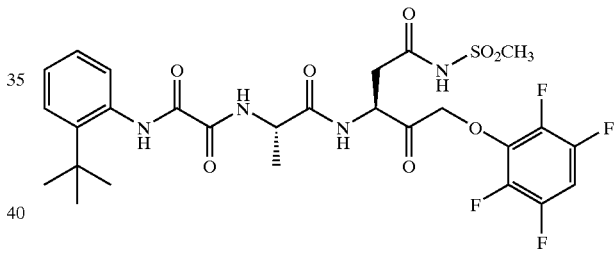

Compound No. 1 was made according to the following reaction scheme, the procedures for which are set forth below.

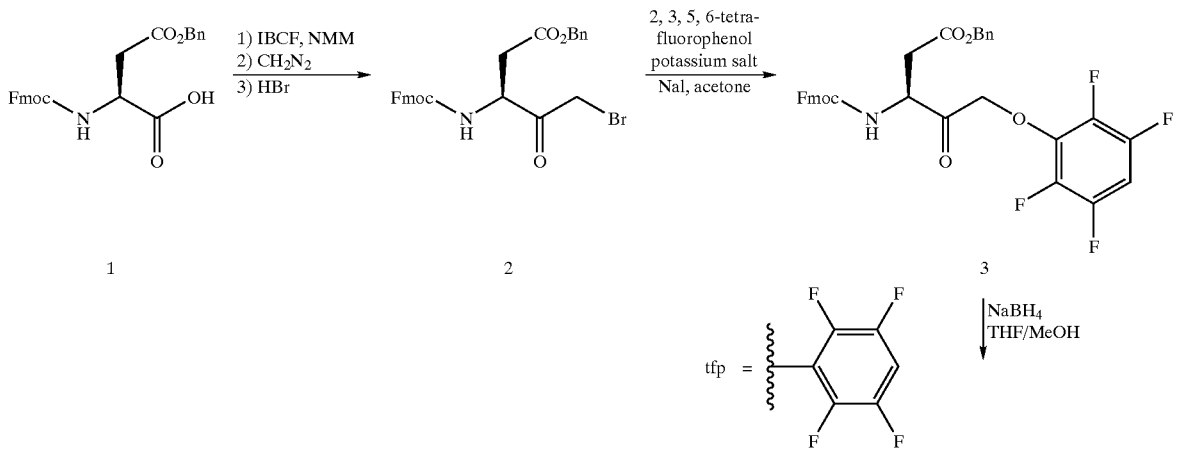

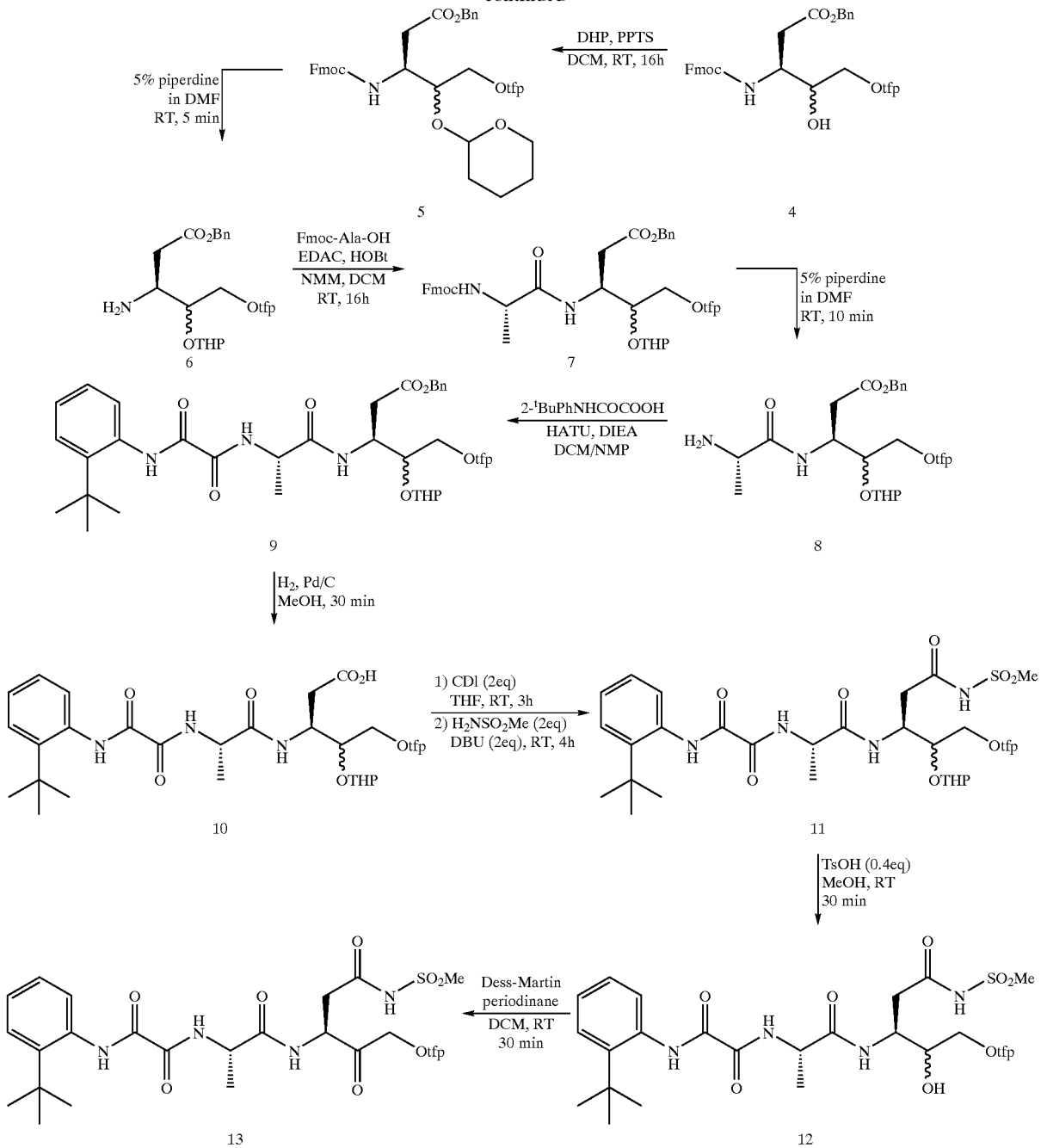

Bromomethylketone 2:

4-Methylmorpholine (0.76 mL, 6.9 mmol) was added to a solution of Fmoc-Asp(OBn)-OH (1) (2.05 g, 4.62 mmol) in 50 mL of dry THF at −10° C. under an atmosphere of nitrogen, followed by the addition of isobutyl chloroformate (0.90 mL, 6.9 mmol), and the solution was stirred for 20 minutes. The resulting white precipitate was removed by filtration and the filtrate was cooled to 0° C. In a separate flask, vb1-methyl-3-nitro-1-nitrosoguanidine (1.10 g, 7.44 mmol) was added to a vigorously stirred mixture of diethyl ether (14 mL) and 40% KOH (8 mL) at 0° C. The resulting mixture was stirred for 10 minutes and the layers were allowed to separate. The ether layer was transferred via plastic pipette to the mixed anhydride in THF and the reaction mixture was stirred for 30 minutes. Then, 48% HBr in water (2.10 mL) was added and the reaction mixture was warmed to room temperature over 15 minutes. The solution was diluted with ethyl acetate, washed twice with saturated aqueous sodium bicarbonate, once with brine, dried (MgSO4), and concentrated. The resulting crude product was purified by flash chromatography on silica gel, eluting with 35% ethyl acetate-hexanes, to afford 1.70 g (71%) of 2 as a white solid. 1H-NMR (300 MHz, CDCl3): d 7.77 (d, J=8 Hz, 2H), 7.58 (d, J=8 Hz, 2H), 7.45–7.29 (m, 9H), 5.77 (d, J=9 Hz, 1H), 5.12 (s, 2H), 4.79–4.71 (m, 1H), 4.63–4.42 (m, 2H), 4.21 (t, J=6 Hz, 1H), 4.04 (s, 2H), 2.97 (ABXq, J=17, 5 Hz, 2H).

Ketone 3:

Sodium iodide (205 mg, 1.37 mmol) was added to a solution of 2 (3.39 g, 6.49 mmol) in 20 mL of acetone at room temperature, followed by the addition of the potassium salt of 2,3,5,6-tetrafluorophenol (1.39 g, 6.82 mmol) and the resulting mixture was stirred for one hour. The reaction mixture was diluted with ethyl acetate, washed twice with brine, dried (MgSO4), and concentrated. The crude product was purified by flash chromatography on silica gel, eluting with 1:1:3 dichloromethane/diethyl ether/hexanes, to provide 3.32 g (84%) of 3 as a white solid. 1H-NMR (300 MHz, CDCl3): d 7.76 (d, J=8 Hz, 2H), 7.58 (d, J=8 Hz, 2H), 7.44–7.27 (m, 9H), 6.85–6.73 (m, 1H), 5.73 (d, J=9 Hz, 1H), 5.15–4.92 (m, 4H), 4.75–4.67 (m, 1H), 4.61–4.42 (m, 2H), 4.21 (t, J=6 Hz, 1H), 3.00 (ABXq, J=18, 4 Hz, 2H).

Alcohol 4:

Sodium borohydride (248 mg, 6.56 mmol) was added to a solution of 3 (608 mg, 5.43 mmol) in 14 mL of dry methanol and 14 mL of dry THF at 0° C. and the resulting mixture was stirred for 30 minutes. The reaction mixture was quenched with saturated aqueous ammonium chloride solution, extracted three times with dichloromethane, and the combined dichloromethane layers were washed once with brine, dried (MgSO4), and concentrated. The crude product was purified by flash chromatography on silica gel, eluting with 50% ethyl acetate-hexanes, to give 2.43 g (73%) of 4 as a white solid. 1H-NMR (300 MHz, CDCl3): d 7.78–7.74 (m, 2H), 7.57 (d, J=7 Hz, 2H), 7.44–7.27 (m, 9H), 6.87–6.75 (m, 1H), 5.62 (d, J=9 Hz, 0.3H), 5.29–5.23 (m, 0.5H), 5.16–5.11 (m, 1H), 4.69 (d, J=6 Hz, 1H), 4.59–4.37 (m, 4H), 4.30–4.04 (m, 3H), 3.35–3.09 (m, 1H), 2.94–2.41 (m, 2H).

THP Ether 5:

3,4-Dihydro-2H-pyran (0.55 mL, 6.0 mmol) and pyridinium p-toluenesulfonate (218 mg, 0.866 mmol) were added to a solution of 4 (2.43 g, 3.99 mmol) in 20 mL of dry dichloromethane and the resulting solution was stirred at room temperature for 16 hours. The reaction mixture was diluted with ethyl acetate, washed twice with saturated aqueous sodium bicarbonate solution, once with brine, dried (MgSO4), and concentrated. The crude product was purified by flash chromatography on silica gel, first eluting with 15% ethyl acetate-hexanes and then with 50% ethyl acetate-hexanes, to afford 1.71 g (62%) of 5 as a colorless oil. 1H-NMR (300 MHz, CDCl3): d 7.76 (d, J=7 Hz, 2H), 7.62–7.55 (m, 2H), 7.42–7.27 (m, 9H), 6.84–6.71 (m, 1H), 6.21 (d, J=9 Hz, 0.3H), 5.65 (d, J=9 Hz, 0.2H), 5.33–5.27 (m, 0.5H), 5.13 (t, J=3 Hz, 2H), 4.72–4.04 (m, 8H), 3.91–3.73 (m, 1H), 3.51–3.36 (m, 1H), 2.98–2.57 (m, 2H), 1.86–1.61 (m, 2H), 1.57–1.43 (m, 4H). (m, 4H).

Amine 6:

Piperidine (0.75 mL, 7.6 mmol) was added to a solution of 5 (1.70 g, 2.45 mmol) in 15 mL of dry DMF at room temperature and the resulting solution was stirred for 5 minutes. The reaction mixture was diluted with ethyl acetate, washed once with saturated aqueous ammonium chloride solution, twice with water, once with brine, dried (MgSO4), and concentrated. The crude product was purified by flash chromatography on silica gel, first eluting with 50% ethyl acetate-hexanes and then with 80% ethyl acetate-hexanes, to provide 793 mg (69%) of 6 as a colorless oil. 1H-NMR (300 MHz, CDCl3): d 7.39–7.29 (m, 5H), 6.82–6.70 (m, 1H), 5.15 (s, 2H), 4.78–4.63 (m, 1H), 4.53–4.26 (m, 2H), 4.03–3.79 (m, 2H), 3.71–3.43 (m, 2H), 2.80–2.43 (m, 2H), 1.85–1.66 (m, 2H), 1.57–1.45 (m, 4H).

Dipeptide 7:

Amine 6 (790 mg, 1.68 mmol) and Fmoc-Ala-OH (578 mg, 1.86 mmol) were dissolved in 40 mL of dry dichloromethane. 1-Hydroxybenzotriazole hydrate (342 mg, 2.53 mmol) was added to this solution, followed by the addition of 4-methylmorpholine (0.30 mL, 2.7 mmol) and 1-(3-dimethylaminopropyl)-3-ethylcarbodiimide hydrochloride (391 mg, 2.04 mmol), and the resulting mixture was stirred at room temperature for 16 hours. The reaction mixture was diluted with ethyl acetate, washed once with saturated aqueous ammonium chloride solution, once with saturated aqueous sodium bicarbonate solution, once with brine, dried (MgSO4), and concentrated. The crude product was purified by flash chromatography on silica gel, eluting with 40% ethyl acetate-hexanes, to give 1.17 g (91%) of 7 as a white solid. 1H-NMR (300 MHz, CDCl3): d 7.76 (d, J=7 Hz, 2H), 7.62–7.55 (m, 2H), 7.40 (t, J=7 Hz, 2H), 7.35–7.28 (m, 4H), 6.95–6.46 (m, 2H), 5.45–5.25 (m, 1H), 5.11–5.05 (m, 2H), 4.75–4.30 (m, 5H), 4.28–4.04 (m, 4H), 3.94–3.76 (m, 1H), 3.50–3.36 (m, 1H), 2.95–2.61 (m, 2H), 1.82–1.65 (m, 2H), 1.54–1.41 (m, 4H), 1.39–1.32 (m, 3H).

Amine 8:

Piperidine (0.50 mL, 5.1 mmol) was added to a solution of 7 (1.17 g, 1.53 mmol) in 10 mL of dry DMF at room temperature and the resulting solution was stirred for 10 minutes. The reaction mixture was diluted with ethyl acetate, washed once with saturated aqueous ammonium chloride solution, twice with water, once with brine, dried (MgSO4), and concentrated. The crude product was purified by flash chromatography on silica gel, first eluting with 50% ethyl acetate-hexanes and then with 20% methanol-dichloromethane, to provide 806 mg (97%) of 8 as a yellow oil. 1H-NMR (300 MHz, CDCl3): d 8.01 (d, J=9 Hz, 0.35H), 7.93 (d, J=9 Hz, 0.24H), 7.64 (d, J=9 Hz, 0.17H), 7.56 (d, J=9 Hz, 0.24H), 7.38–7.28 (m, 5H), 6.83–6.70 (m, 1H), 5.17–5.06 (m, 2H), 4.76–4.24 (m, 4H), 4.23–4.03 (m, 1H), 3.91–3.79 (m, 1H), 3.51–3.38 (m, 2H), 2.95–2.61 (m, 2H), 1.85–1.66 (m, 2H), 1.59–1.41 (m, 4H), 1.29–1.25 (m, 3H).

Oxamide 9:

O-(7-Azabenzotriazol-1-yl)-N,N,N',N'-tetramethyluronium hexafluorophosphate (308 mg, 0.809 mmol) was added to 2-t-butylphenyloxamic acid (150 mg, 0.678 mmol) in 0.75 mL of dry NMP and 1.5 mL of dry dichloromethane at room temperature. The mixture was stirred for 15 minutes, and then a solution of 8 (365 mg, 0.672 mmol) in 1.5 mL of dry dichloromethane was added, followed by the addition of diisopropylethyl amine (0.35 mL, 2.0 mmol). The reaction mixture was stirred for 14 hours, diluted with ethyl acetate, washed once with saturated aqueous ammonium chloride solution, once with saturated aqueous sodium bicarbonate solution, once with brine, dried (MgSO4), and concentrated. The crude product was purified by flash chromatography, eluting with 35% ethyl acetate-hexanes, to give 315 mg (63%) of 9 as a colorless oil. 1H-NMR (300 MHz, CDCl3): d 9.57 (s, 0.4H), 9.54 (s, 0.6H), 8.11–7.95 (m, 2H), 7.44–7.24 (m, 7H), 7.21–7.13 (m, 1H), 6.96–6.50 (m, 2H), 5.13–5.07 (m, 2H), 4.77–4.05 (m, 6H), 3.97–3.77 (m, 1H), 3.55–3.39 (m, 1H), 2.96–2.62 (m, 2H), 1.85–1.61 (m, 2H), 1.55–1.37 (m, 16H). Acid 10:

10% Palladium on carbon (76 mg) was added to a solution of 9 (300 mg, 0.402 mmol) in anhydrous methanol (7 mL) under an atmosphere of nitrogen and the flask was then evacuated with the house vacuum. The mixture was stirred under a balloon of hydrogen gas for 30 minutes, then filtered through Celite, and eluted with methanol. The solution was concentrated to afford 249 mg (94%) of 10 as a white solid.

Methyl Sulfonimide 11:

1,1'-Carbonyldiimidazole (124 mg, 0.766 mmol) was added to a solution of 10 (249 mg, 0.380 mmol) in dry THF (6 mL) under an atmosphere of nitrogen, and the reaction mixture was stirred for 3 hours. The mixture was cooled to 0° C., and the methanesulfonamide (73 mg, 0.77 mmol) was added, followed by the addition of 1,8-diazabicyclo[5.4.0]undec-7-ene (0.115 mL, 0.77 mmol). The resulting mixture was stirred at room temperature for 4 hours. The reaction mixture was diluted with ethyl acetate, washed once with 1 N HCl solution, twice with water, once with brine, dried (MgSO4), and concentrated. The residue was reconcentrated from dichloromethane to provide 271 mg (97%) of 11 as a white solid. 1H-NMR (300 MHz, CDCl3): d 9.59–9.48 (m, 1H), 8.25–8.15 (m, 1H), 7.95–7.88 (m, 1H), 7.69 (d, J=8 Hz, 0.3H), 7.44–7.38 (m, 1H), 7.28–7.13 (m, 2.4H), 6.93–6.87 (m, 0.3H), 6.85–6.71 (m, 1H), 4.75–4.33 (m, 4H), 4.27–4.01 (m, 3H), 3.87–3.43 (m, 1H), 3.28–3.23 (m, 3H), 2.93–2.56 (m, 2H), 1.86–1.68 (m, 2H), 1.55–1.39 (m, 16H).

Alcohol 12:

p-Toluenesulfonic acid (21 mg, 0.11 mmol) was added to a solution of 11 (202 mg, 0.275 mmol) in anhydrous methanol (3 mL) and the reaction mixture was stirred at room temperature for 30 minutes. The mixture was diluted with ethyl acetate, washed three times with water, once with brine, dried (MgSO4), and concentrated to afford 166 mg (93%) of 12 as a white solid. 1H-NMR (300 MHz, CDCl3): d 9.57–9.46 (m, 1H), 8.34 (t, J=8 Hz, 1H), 7.80 (d, J=8 Hz, 1H), 7.44–7.30 (m, 2H), 7.23–7.12 (m, 2H), 6.83–6.69 (m, 1H), 4.66–4.45 (m, 3H), 4.33–4.10 (m, 3H), 3.26 (s, 1.2H), 3.25 (s, 1.8H), 2.90–2.76 (m, 2H), 1.48–1.38 (m, 12H).

Methylsulfonimide 13 ("Compound No. 1"):

Dess-Martin periodinane (126 mg, 0.297 mmol) was added to a solution of 12 (154 mg, 0.238 mmol) in 5 mL of dry dichloromethane, and the reaction mixture was stirred at room temperature for 30 minutes. The mixture was diluted with ethyl acetate, washed twice with water, once with brine, dried (MgSO$_4$), and concentrated. The crude product was purified by flash chromatography, eluting first with 60% ethyl acetate-hexanes and then with 80% ethyl acetate-hexanes, to provide 114 mg (74%) of 13 as a white solid. $^1$H-NMR (300 MHz, CDCl$_3$): δ 9.53 (s, 1H), 8.27–7.87 (m, 2H), 7.42 (d, J=8 Hz, 1H), 7.29–7.15 (m, 2H), 6.92–6.77 (m, 2H), 5.02–4.77 (m, 3H), 4.56–4.27 (m, 2H), 3.37 (s, 3H), 3.06–2.60 (m, 2H), 1.56–1.42 (m, 12H); MS (ESI)m/ 645 [(M+)−1].

EXAMPLE 3

Representative Compounds

The representative compounds listed in the following Table 1 may be made according to the procedures set forth in Example 2.

TABLE 1

Representative Compounds

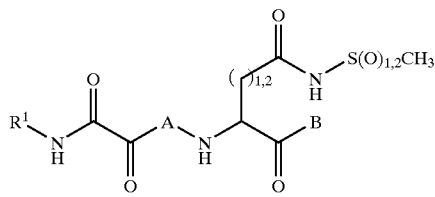

| Cpd | A | B | R$^1$ |
|---|---|---|---|
| 1 | NHCH(CH$_2$CH(CH$_3$)$_2$)CO | H | 1-naphthyl |
| 2 | NHCH(CH$_2$CH(CH$_3$)$_2$)CO | CH$_2$F | 1-naphthyl |
| 3 | NHCH(CH(CH$_3$)$_2$)CO | CH$_2$F | 1-naphthyl |
| 4 | NHCH(CH(CH$_3$)$_2$)CO | CH$_2$OCO(2,4-diCl—Ph) | 1-naphthyl |
| 5 | NHCH(CH(CH$_3$)$_2$)CO | CH$_2$O(2,6-diF—Ph) | 1-naphthyl |
| 6 | NHCH(CH(CH$_3$)$_2$)CO | CH$_2$O(2,4,6-triF—Ph) | 1-naphthyl |
| 7 | NHCH(CH(CH$_3$)$_2$)CO | CH$_2$O(2,3,5,6-tetraF—Ph) | 1-naphthyl |
| 8 | NHCH(CH(CH$_3$)$_2$)CO | CH$_2$O(6-Me-2-pyron-4-yl) | 1-naphthyl |
| 9 | NHCH(CH(CH$_3$)$_2$)CO | CH$_2$O(2-Ph-5,6-benzopyran-4-on-3-yl) | 1-naphthyl |
| 10 | NHCH(CH(CH$_3$)$_2$)CO | CH$_2$OPO(Me)Ph | 1-naphthyl |
| 11 | NHCH(CH(CH$_3$)$_2$)CO | CH$_2$OPOPh$_2$ | 1-naphthyl |
| 12 | NHCH(CH(CH$_3$)$_2$)CO | CH$_2$O(2-CF$_3$-pyrimidin-4-yl) | 1-naphthyl |
| 13 | NHCH(CH(CH$_3$)$_2$)CO | CH$_2$O(5-CO$_2$Me-isoxazol-3-yl) | 1-naphthyl |
| 14 | NHCH(CH(CH$_3$)$_2$)CO | CH$_2$OPO(Me)(1-naphthyl) | 1-naphthyl |
| 15 | NHCH(CH$_2$CH(CH$_3$)$_2$)CO | CH$_2$OPOPh$_2$ | 1-naphthyl |
| 16 | NHCH(CH$_2$CH(CH$_3$)$_2$)CO | CH$_2$OCO(2,6-diCl—Ph) | 1-naphthyl |
| 17 | NHCH(CH$_2$CH(CH$_3$)$_2$)CO | CH$_2$O(2,4,6-triF—Ph) | 1-naphthyl |
| 18 | NHCH(CH$_2$CH(CH$_3$)$_2$)CO | CH$_2$O(2,3,5,6-tetraF—Ph) | 1-naphthyl |
| 19 | NHCH(CH$_2$CH(CH$_3$)$_2$)CO | CH$_2$OPO(Me)Ph | 1-naphthyl |
| 20 | NHCH(CH$_3$)CO | CH$_2$O(2-F—Ph) | (2-Ph)Ph |
| 21 | NHCH(CH$_3$)CO | CH$_2$OCO(2,6-di-Cl—Ph) | (2-Ph)Ph |
| 22 | NHCH(CH$_3$)CO | CH$_2$OPOPh$_2$ | (2-Ph)Ph |
| 23 | NHCH(CH$_3$)CO | CH$_2$O(2-F—Ph) | (2-t-Bu)Ph |
| 24 | NHCH(CH$_3$)CO | CH$_2$OPOPh$_2$ | (2-t-Bu)Ph |
| 25 | NHCH(CH$_3$)CO | CH$_2$OCO(2,3,5,6-tetra-Cl—Ph) | 1-naphthyl-CH$_2$ |
| 26 | NHCH(CH$_3$)CO | CH$_2$OCO(2,6-di-Cl—Ph) | 1-naphthyl-CH$_2$ |
| 27 | NHCH(CH$_3$)CO | CH$_2$OPOPh$_2$ | 1-naphthyl-CH$_2$ |
| 28 | NHCH(CH(CH$_3$)$_2$)CO | CH$_2$O(2,3,5,6-tetraF—Ph) | 1-naphthyl-CH$_2$ |
| 29 | NHCH(CH(CH$_3$)$_2$)CO | CH$_2$O(2,3,5,6-tetraF—Ph) | PhCH$_2$ |
| 30 | NHCH(CH(CH$_3$)$_2$)CO | CH$_2$O(2,3,5,6-tetraF—Ph) | Ph(CH$_2$)$_2$ |
| 31 | NHCH(CH(CH$_3$)$_2$)CO | CH$_2$O(2,3,5,6-tetraF—Ph) | Ph$_2$CH |
| 32 | NHCH(CH(CH$_3$)$_2$)CO | CH$_2$O(2,3,5,6-tetraF—Ph) | Ph |

TABLE 1-continued

Representative Compounds $$R^1 \text{—NH—CO—CO—A—NH—CH(B)—CO—NH—(CH}_2)_{1,2}\text{—CO—NH—S(O)}_{1,2}\text{CH}_3$$

| Cpd | A | B | R¹ |
|---|---|---|---|
| 33 | NHCH(CH(CH₃)₂)CO | CH₂O(2,3,5,6-tetraF—Ph) | (2-Ph)Ph |
| 34 | NHCH(CH(CH₃)₂)CO | CH₂O(2,3,5,6-tetraF—Ph) | (2-PhCH₂)Ph |
| 35 | NHCH(CH(CH₃)₂)CO | CH₂O(2,3,5,6-tetraF—Ph) | (3-PhO)Ph |
| 36 | NHCH(CH(CH₃)₂)CO | CH₂O(2,3,5,6-tetraF—Ph) | 4-Cl-1-naphthyl |
| 37 | NHCH(CH(CH₃)₂)CO | CH₂O(2,3,5,6-tetraF—Ph) | 2-anthryl |
| 38 | NHCH(CH(CH₃)₂)CO | CH₂O(2,3,5,6-tetraF—Ph) | 2-benzimidazolyl |
| 39 | NHCH(CH(CH₃)₂)CO | CH₂O(2,3,5,6-tetraF—Ph) | 1-adamantanyl |
| 40 | NHCH(CH(CH₃)₂)CO | CH₂O(2,3,5,6-tetraF—Ph) | (2-F)Ph |
| 41 | NHCH(CH(CH₃)₂)CO | CH₂O(2,3,5,6-tetraF—Ph) | (4-F)Ph |
| 42 | NHCH(CH(CH₃)₂)CO | CH₂O(2,3,5,6-tetraF—Ph) | (2-CF₃)Ph |
| 43 | NHCH(CH(CH₃)₂)CO | CH₂O(2,3,5,6-tetraF—Ph) | (2-t-Bu)Ph |
| 44 | NHCH(CH(CH₃)₂)CO | CH₂O(2,3,5,6-tetraF—Ph) | (4-n-heptyl)Ph |
| 45 | NHCH(CH(CH₃)₂)CO | CH₂O(2,3,5,6-tetraF—Ph) | (2-CH₃O)Ph |
| 46 | NHCH(CH(CH₃)₂)CO | CH₂O(2,3,5,6-tetraF—Ph) | (2-PhO)Ph |
| 47 | NHCH(CH(CH₃)₂)CO | CH₂O(2,3,5,6-tetraF—Ph) | 2-naphthyl |
| 48 | NHCH(CH(CH₃)₂)CO | CH₂O(2,3,5,6-tetraF—Ph) | 5,6,7,8-tetrahydro-1-naphthyl |
| 49 | NHCH(CH(CH₃)₂)CO | CH₂O(2,3,5,6-tetraF—Ph) | 1-anthryl |
| 50 | NHCH(CH(CH₃)₂)CO | CH₂O(2,3,5,6-tetraF—Ph) | 2-pyridinyl |
| 51 | NHCH(CH(CH₃)₂)CO | CH₂O(2,3,5,6-tetraF—Ph) | 4-pyridinyl |
| 52 | NHCH(CH(CH₃)₂)CO | CH₂O(2,3,5,6-tetraF—Ph) | 2,3,5,6-tetrafluoro-4-pyridinyl |
| 53 | NHCH(CH(CH₃)₂)CO | CH₂O(2,3,5,6-tetraF—Ph) | 2-pyrazinyl |
| 54 | NHCH(CH(CH₃)₂)CO | CH₂O(2,3,5,6-tetraF—Ph) | 1,2,3,4-tetrahydro-1-naphthyl |
| 55 | NHCH(CH(CH₃)₂)CO | CH₂O(2,3,5,6-tetraF—Ph) | (2-Cl)Ph |
| 56 | NHCH(CH(CH₃)₂)CO | CH₂O(2,3,5,6-tetraF—Ph) | (2-Br)Ph |
| 57 | NHCH(CH(CH₃)₂)CO | CH₂O(2,3,5,6-tetraF—Ph) | (2-I)Ph |
| 58 | NHCH(CH(CH₃)₂)CO | CH₂O(2,3,5,6-tetraF—Ph) | (2,6-di-F)Ph |
| 59 | NHCH(CH(CH₃)₂)CO | CH₂O(2,3,5,6-tetraF—Ph) | (2,5-di-t-Bu)Ph |
| 60 | NHCH(CH(CH₃)₂)CO | CH₂O(2,3,5,6-tetraF—Ph) | 5-indanyl |
| 61 | NHCH(CH(CH₃)₂)CO | CH₂O(2,3,5,6-tetraF—Ph) | (3,4,5-tri-MeO)PhCH₂ |
| 62 | NHCH(CH(CH₃)₂)CO | CH₂O(2,3,5,6-tetraF—Ph) | methyl |
| 63 | NHCH(CH(CH₃)₂)CO | CH₂O(2,3,5,6-tetraF—Ph) | n-heptyl |
| 64 | NHCH(CH(CH₃)₂)CO | CH₂O(2,3,5,6-tetraF—Ph) | t-octyl |
| 65 | NHCH(CH(CH₃)₂)CO | CH₂O(2,3,5,6-tetraF—Ph) | cyclo-hexyl |
| 66 | NHCH(CH(CH₃)₂)CO | CH₂O(2,3,5,6-tetraF—Ph) | 5-Ph-3-pyrazolyl |
| 67 | NHCH(CH(CH₃)₂)CO | CH₂O(2,3,5,6-tetraF—Ph) | (2-F-4-I)Ph |
| 68 | NHCH(CH(CH₃)₂)CO | CH₂O(2,3,5,6-tetraF—Ph) | (2,3,4,5-tetra-F)Ph |
| 69 | NHCH(CH(CH₃)₂)CO | CH₂O(2,3,5,6-tetraF—Ph) | (2,3,4,6-tetra-F)Ph |
| 70 | NHCH(CH(CH₃)₂)CO | CH₂O(2,3,5,6-tetraF—Ph) | (2,3,5,6-tetra-Cl)Ph |
| 71 | NHCH(CH(CH₃)₂)CO | CH₂O(2,3,5,6-tetraF—Ph) | (2,3,4,5,6-penta-F)Ph |
| 72 | NHCH(CH(CH₃)₂)CO | CH₂O(2,3,5,6-tetraF—Ph) | Ph₂N |
| 73 | NHCH(CH(CH₃)₂)CO | CH₂O(2,3,5,6-tetraF—Ph) | PHCH₂(Ph)N |
| 74 | NHCH(CH(CH₃)₂)CO | CH₂O(2,3,5,6-tetraF—Ph) | PhCH₂O |
| 75 | NHCH(CH₃)CO | CH₂O(2,3,5,6-tetraF—Ph) | (2-t-Bu)Ph |
| 76 | NHCH(CH₃)CO | CH₂O(2,3,5,6-tetraF—Ph) | (2-CF₃)Ph |
| 77 | NHCH(CH₃)CO | CH₂O(2,3,5,6-tetraF—Ph) | (2-Ph)Ph |
| 78 | NHCH(CH₃)CO | CH₂O(2,3,5,6-tetraF—Ph) | (2-PhCH₂)Ph |
| 79 | NHCH(CH₃)CO | CH₂O(2,3,5,6-tetraF—Ph) | (2-PhO)Ph |
| 80 | NHCH(CH₃)CO | CH₂O(2,3,5,6-tetraF—Ph) | (3-PhO)Ph |
| 81 | NHCH(CH₃)CO | CH₂O(2,3,5,6-tetraF—Ph) | 5,6,7,8-tetrahydro-1-naphthyl |
| 82 | NHCH(CH₃)CO | CH₂O(2,3,5,6-tetraF—Ph) | 1-naphthyl |
| 83 | NHCH(CH₃)CO | CH₂O(2,3,5,6-tetraF—Ph) | Ph |
| 84 | NHCH(CH₃)CO | CH₂O(2,3,5,6-tetraF—Ph) | (2,6-di-F)Ph |
| 85 | NHCH(CH₃)CO | CH₂O(2,3,5,6-tetraF—Ph) | (4-Ph)Ph |
| 86 | NHCH(CH₃)CO | CH₂O(2,3,5,6-tetraF—Ph) | (4-MeO)Ph |
| 87 | NHCH(CH₃)CO | CH₂O(2,3,5,6-tetraF—Ph) | Ph₂CH |
| 88 | NHCH(CH₂cyclohexyl)CO | CH₂O(2,3,5,6-tetraF—Ph) | (2-PhO)Ph |
| 89 | NHCH(CH₂cyclohexyl)CO | CH₂O(2,3,5,6-tetraF—Ph) | (2-Ph)Ph |
| 90 | NHCH(CH₂cyclohexyl)CO | CH₂O(2,3,5,6-tetraF—Ph) | (2-PhCH₂)Ph |
| 91 | NHCH(CH₂cyclohexyl)CO | CH₂O(2,3,5,6-tetraF—Ph) | 1-naphthyl |

TABLE 1-continued

Representative Compounds

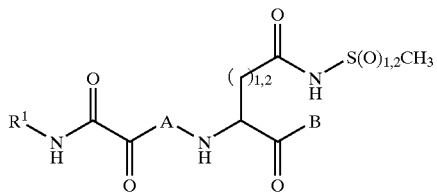

| Cpd | A | B | R¹ |
|---|---|---|---|
| 92 | NHCH(CH₂cyclohexyl)CO | CH₂OCO(2,6-diCl—Ph) | 5,6,7,8-tetrahydro-1-naphthyl |
| 93 | NHCH(CH₂cyclohexyl)CO | CH₂O(2,3,5,6-tetra-F—Ph) | 5,6,7,8-tetrahydro-1-naphthyl |
| 94 | NHCH(CH₂cyclohexyl)CO | CH₂OPO(Me)Ph | 5,6,7,8-tetrahydro-1-naphthyl |
| 95 | NHCH(CH₂cyclohexyl)CO | CH₂OPOPh₂ | 5,6,7,8-tetrahydro-1-naphthyl |
| 96 | NHCH(CH₂cyclohexyl)CO | CH₂OPO(Me)Ph | (2-PhCH₂)Ph |
| 97 | NHCH(CH₂cyclohexyl)CO | CH₂OPOPh₂ | (2-PhCH₂)Ph |
| 98 | NHCH(CH₂cyclohexyl)CO | CH₂OPO(Me)Ph | (2-Ph)Ph |
| 99 | NHCH(CH₂cyclohexyl)CO | CH₂OPOPh₂ | (2-Ph)Ph |
| 100 | (3-piperidinylcarbonyl) | CH₂O(2,3,5,6-tetra-F—Ph) | 1-naphthyl |
| 101 | (indoline-3-carbonyl) | CH₂O(2,3,5,6-tetra-F—Ph) | 1-naphthyl |
| 102 | NHCH(cyclohexyl)CO | CH₂O(2,3,5,6-tetra-F—Ph) | 1-naphthyl |
| 103 | norleucine | CH₂O(2,3,5,6-tetra-F—Ph) | 1-naphthyl |
| 104 | (t-butyl)glycine | CH₂O(2,3,5,6-tetra-F—Ph) | 1-naphthyl |
| 105 | (t-butyl)alanine | CH₂O(2,3,5,6-tetra-F—Ph) | 1-naphthyl |
| 106 | phenylglycine | CH₂O(2,3,5,6-tetra-F—Ph) | 1-naphthyl |
| 107 | phenylalanine | CH₂O(2,3,5,6-tetra-F—Ph) | 1-naphthyl |
| 108 | homophenylalanine | CH₂O(2,3,5,6-tetra-F—Ph) | 1-naphthyl |
| 109 | 1-aminocyclopentane carboxylic acid | CH₂O(2,3,5,6-tetra-F—Ph) | 1-naphthyl |
| 110 | NHCH(CH₂CH₂SOCH₃)CO | CH₂O(2,3,5,6-tetra-F—Ph) | 1-naphthyl |
| 111 | (3-piperidinylcarbonyl) | H | 1-naphthyl |
| 112 | NHCH(CH(CH₃)₂)CO | H | 2-(1H-tetrazol-5-yl)Ph |
| 113 | NHCH(CH(CH₃)₂)CO | H | 1-adamantanyl |
| 114 | NHCH(CH(CH₃)₂)CO | H | Ph |
| 115 | NHCH(CH(CH₃)₂)CO | H | PhCH₂ |
| 116 | NHCH(CH(CH₃)₂)CO | H | Ph(CH₂)₂ |
| 117 | NHCH(CH(CH₃)₂)CO | H | (2-CF₃)Ph |
| 118 | NHCH(CH(CH₃)₂)CO | H | (2-t-Bu)Ph |
| 119 | NHCH(CH(CH₃)₂)CO | H | (2-Ph)Ph |
| 120 | NHCH(CH(CH₃)₂)CO | H | (2-PhCH₂)Ph |
| 121 | NHCH(CH(CH₃)₂)CO | H | (2-PhO)Ph |
| 122 | NHCH(CH(CH₃)₂)CO | H | 2-naphthyl |
| 123 | NHCH(CH(CH₃)₂)CO | H | 1-naphthyl |
| 124 | NHCH(CH(CH₃)₂)CO | H | 4-Cl-1-naphthyl |

TABLE 1-continued

Representative Compounds

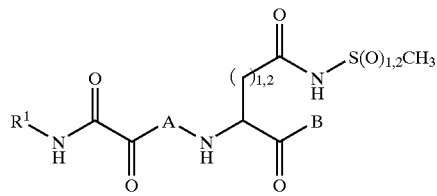

| Cpd | A | B | R[1] |
|---|---|---|---|
| 125 | NHCH(CH(CH$_3$)$_2$)CO | H | 5,6,7,8-tetrahydro-1-naphthyl |
| 126 | NHCH(CH(CH$_3$)$_2$)CO | H | 1,2,3,4-tetrahydro-1-naphthyl |
| 127 | NHCH(CH(CH$_3$)$_2$)CO | H | (1-naphthyl)CH$_2$ |

EXAMPLE 4

Activity of Representative Compound

The activity of a representative compound of this invention (i.e., Compound No. 1) evaluated according to the procedures disclosed in Example 1. More specifically, the ions set forth in Example 1 were used determine the $K_i$ values of inhibitor (i.e., Compound No. 1) bound to a ICE/ced-3 family protease. A continuous assay was run for sixty minutes at various concentrations of the inhibitor and the substrate. The assay was formulated essentially the same as described in Example 1, except that the reaction was initiated by adding the enzyme to the substrate-inhibitor mixture. The $K_i$ values were obtained by simulating the product AMC formation as a function of time according to Equation 1. The results of this assay are set forth below in Table 1, wherein the reference compound was Cbz-ValAlaAsp-CH$_2$F

TABLE 2

| Cpd. No. | mICE $K_i(\mu M)$ | CPP32 $K_i(\mu M)$ | MCH-2 $K_i(\mu M)$ | MCH-5 $K_i(\mu M)$ |
|---|---|---|---|---|
| 1 | 0.004 | 0.856 | 0.681 | 0.011 |
| reference | 0.015 | 0.820 | 0.594 | 0.018 |

Although the invention has been described with reference to the examples provided above, it should be understood that various modifications can be made without departing from the spirit of the invention. Accordingly, the invention is limited only by the claims.

---

We claim:
1. A compound of the following formula:

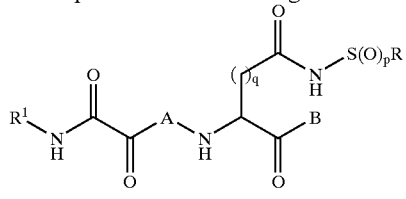

wherein:

p is 1 or 2;

q is 1 or 2;

R and $R^1$ are the same or different and independently alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, substituted (heteroaryl)alkyl, $R^{1a}(R^{1b})N$ or $R^{1c}O$;

A is a natural or unnatural amino acid of Formula IIa–i:

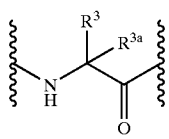

IIa

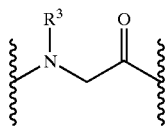

IIb

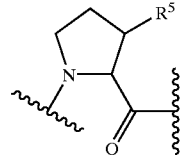

IIc

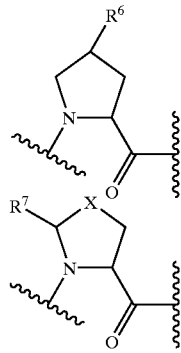

IId

IIe

IIf

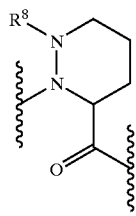

IIg

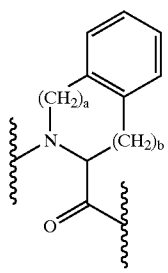

IIh

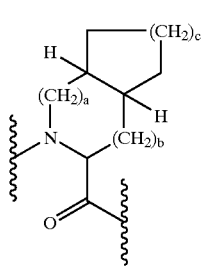

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, $(CH_2)_n$cycloalkyl, $(CH_2)_n$phenyl, $(CH_2)_n$(substituted phenyl), $(CH_2)_n$(1 or 2-naphthyl), $(CH_2)_n$(substituted 1 or 2-naphthyl), $(CH_2)_n$(heteroaryl), $(CH_2)_n$(substituted heteroaryl), halomethyl, $CO_2R^{12}$, $CONR^{13}R^{14}$, $CH_2ZR^{15}$, $CH_2OCO$(aryl), $CH_2OCO$(heteroaryl), or $CH_2OPO(R^{16})R^{17}$, where Z is an oxygen or a sulfur atom, or B is a group of the Formula IIIa–c:

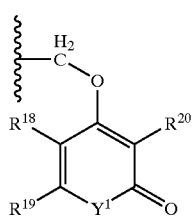

IIIa

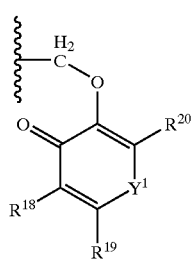

IIIb

-continued

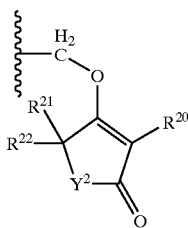
IIIc and wherein:

$R^{1a}$ and $R^{1b}$ are the same or different and, at each occurrence, independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl, with the proviso that $R^{1a}$ and $R^{1b}$ cannot both be hydrogen;

$R^{1c}$ is, at each occurrrence, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl;

$R^3$ is $C_{1-6}$ lower alkyl, cycloalkyl, phenyl, substituted phenyl, $(CH_2)_nNH_2$, $(CH_2)_nNHCOR^9$, $(CH_2)_nN(C=NH)NH_2$, $(CH_2)_mCO_2R^2$, $(CH_2)_mOR^{10}$, $(CH_2)_mSR^{11}$, $(CH_2)_n$cycloalkyl, $(CH_2)_n$phenyl, $(CH_2)_n$(substituted phenyl), $(CH_2)_n$(1 or 2-naphthyl) or $(CH_2)_n$(heteroaryl);

$R^{3a}$ is hydrogen or methyl, or $R^3$ and $R^{3a}$ taken together are —$(CH_2)_d$— where d is an interger from 2 to 6;

$R^4$ is phenyl, substituted phenyl, $(CH_2)_m$phenyl, $(CH_2)_m$(substituted phenyl), cycloalkyl, or benzofused cycloalkyl;

$R^5$ is hydrogen, lower alkyl, cycloalkyl, phenyl, substituted phenyl, $(CH_2)_n$cycloalkyl, $(CH_2)_n$phenyl, $(CH_2)_n$(substituted phenyl), or $(CH_2)_n$(1 or 2-naphthyl);

$R^6$ is hydrogen, fluorine, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, $SR^{11}$ or $NHCOR^9$;

$R^7$ is hydrogen, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^8$ is lower alkyl, cycloalkyl, $(CH_2)_n$cycloalkyl, $(CH_2)_n$phenyl, $(CH_2)_n$(substituted phenyl), $(CH_2)_n$(1 or 2-naphthyl), or $COR^9$;

$R^9$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{12}$, or $NR^{13}R^4$;

$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{12}$ is lower alkyl, cycloalkyl, $(CH_2)_n$cycloalkyl, $(CH_2)_n$phenyl, $(CH_2)_n$(substituted phenyl), or $(CH_2)_n$(1 or 2-naphthyl);

$R^{13}$ is hydrogen, lower alkyl, cycloalkyl, phenyl, substituted phenyl, naphthyl, substituted naphthyl, $(CH_2)_n$cycloalkyl, $(CH_2)_n$phenyl, $(CH_2)_n$(substituted phenyl), or $(CH_2)_n$(1 or 2-naphthyl);

$R^{14}$ is hydrogen or lower alkyl;

or $R^{13}$ and $R^{14}$ taken together form a five to seven membered carbocyclic or heterocyclic ring;

$R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);

$R^{16}$ and $R^{17}$ are independently lower alkyl, cycloalkyl, phenyl, substituted phenyl, naphthyl, phenylalkyl, substituted phenylalkyl, or (cycloalkyl)alkyl;

$R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are —$(CH=CH)_2$—;

$R^{20}$ is hydrogen, alkyl, phenyl, substituted phenyl, $(CH_2)_n$phenyl, $(CH_2)_n$(substituted phenyl);

$R^{21}$, $R^{22}$ and $R^{23}$ are independently hydrogen, or alkyl;

X is $CH_2$, $(CH_2)_2$, $(CH_2)_3$, or S;

$Y^1$ is O or $NR^{23}$;

$Y^2$ is $CH_2$, O, or $NR^{23}$;

a is 0 or 1 and b is 1 or 2, provided that when a is 1 then b is 1;

c is 1 or 2, provided that when c is 1 then a is 0 and b is 1;

m is 1 or 2; and n is 1,2,3 or 4;

or a salt thereof.

2. The compound of claim 1 wherein A is

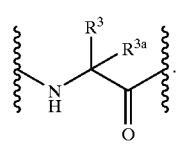
IIa

3. The compound of claim 2 wherein $R^3$ is lower alkyl, cycloalkyl, phenyl, $(CH_2)_nNH_2$, $(CH_2)_mOR^{10}$, $(CH_2)_mSR^{11}$, $(CH_2)_n$cycloalkyl, $(CH_2)_n$phenyl, $(CH_2)_n$(substituted phenyl), or $(CH_2)_n$(1 or 2-naphthyl); and $R^{3a}$ is hydrogen.

4. The compound of claim 1 wherein A is

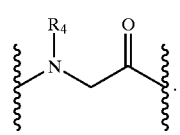
IIb

5. The compound of claim 4 wherein $R^4$ is phenyl, substituted phenyl, $(CH_2)_m$phenyl, $(CH_2)_m$(substituted phenyl), cycloalkyl, or 2-indanyl.

6. The compound of claim 1 wherein A is

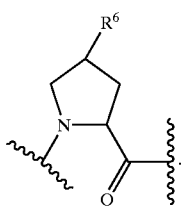
IId

7. The compound of claim 6 wherein $R^6$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$.

8. The compound of claim 1 wherein A is

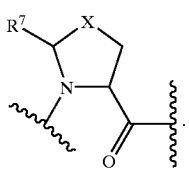
IIe

9. The compound of claim 8 wherein $R^7$ is hydrogen, oxo, cycloalkyl, phenyl, substituted phenyl, or naphthyl; and $X=CH_2$, $(CH_2)_2$, $(CH_2)_3$, or $S$.

10. The compound of claim 1 wherein A is

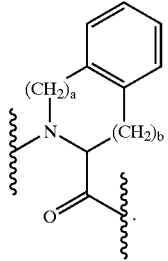
IIh

11. The compound of claim 10 wherein a is 0.

12. The compound of claim 1 wherein B is hydrogen, 2-benzoxazolyl, substituted 2-oxazolyl, $CH_2ZR^{15}$, $CH_2OCO$(aryl), or $CH_2OPO(R^{16})R^{17}$, and wherein Z is an oxygen or a sulfur atom.

13. The compound of claim 1 wherein B is

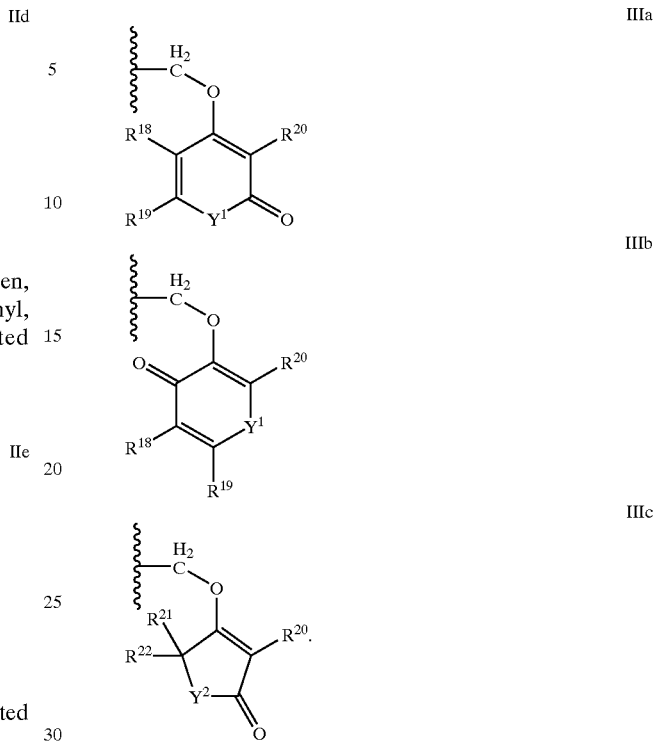

IIIa

IIIb

IIIc

14. The compound of claim 13 wherein $R^{18}$ and $R^{19}$ are independently hydrogen, alkyl, or phenyl, or wherein $R^{18}$ and $R^{19}$ taken together are —(CH=CH)$_2$—.

15. The compound of claim 1 wherein $R^1$ is phenyl, substituted phenyl, phenylalkyl, substituted phenylalkyl, naphthyl, substituted naphthyl, (1 or 2 naphthyl)alkyl, heteroaryl, or (heteroaryl)alkyl.

16. The compound of claim 3 wherein $R^3$ is methyl, isopropyl, isobutyl, cyclohenxylmethyl, t-butyl, cycohexyl or phenyl.

17. The compound of claim 16 wherein B is CH$_2$O(2,3,5,6-tetrafluorophenyl).

18. The compound of claim 1 wherein $R^1$ is 1-naphthyl and A is valine.

19. The compound of claim 1 wherein $R^1$ is 1-naphthyl and B is CH$^2$O(2,3,5,6-tetrafluorophenyl).

20. The compound of claim 1 wherein R is lower alkyl.

21. The compound of claim 1 wherein R is methyl.

22. The compound of claim 1 wherein q is 1.

23. The compound of claim 1 wherein p is 2.

24. A composition comprising an acceptable carrier and a compound of claim 1 in an amount effective to inhibit a caspase.

* * * * *

UNITED STATES PATENT AND TRADEMARK OFFICE
CERTIFICATE OF CORRECTION

PATENT NO.   : 6,515,173 B1
DATED        : February 4, 2003
INVENTOR(S)  : Robert J. Ternansky et al.

It is certified that error appears in the above-identified patent and that said Letters Patent is hereby corrected as shown below:

<u>Title page,</u>
Item [57], ABSTRACT, "This invention s directed to" should read -- This invention is directed to --.
"wherein A, B, R, $R_1$, p and q are as defined herein. The invention s all directed to pharmaceutical compositions containing one or more of thee compound, as well as to the use of such compositions in the treatment of patients suffering inflammatory, autoimmune and neurodegenerative diseases, for the prevention of ischemic injury, and for the preservation of organs that undergo a transplantation procedure" should read -- wherein A, B, R, $R_1$, p and q are as defined herein. The invention is also directed to pharmaceutical compositions containing one or more of these compounds, as well as to the use of such compositions in the treatment of patients suffering inflammatory, autoimmune and neurodegenerative diseases, for the prevention of ischemic injury, and for the preservation of organs that are to undergo a transplantation procedure. --.

<u>Column 33, lines 26-67 through Column 34, lines 1-34,</u>

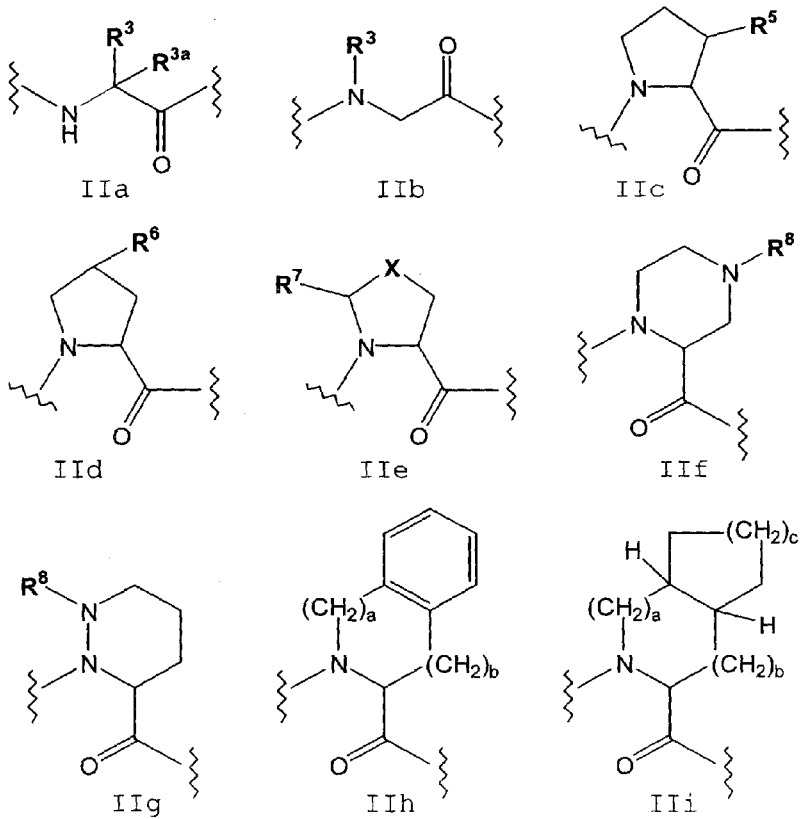

UNITED STATES PATENT AND TRADEMARK OFFICE
CERTIFICATE OF CORRECTION

PATENT NO.   : 6,515,173 B1  
DATED        : February 4, 2003  
INVENTOR(S)  : Robert J. Ternansky et al.

It is certified that error appears in the above-identified patent and that said Letters Patent is hereby corrected as shown below:

should read --

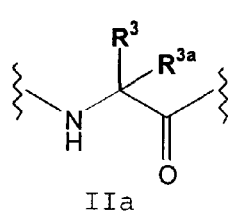 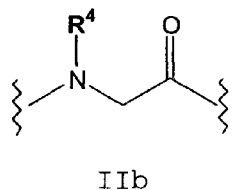 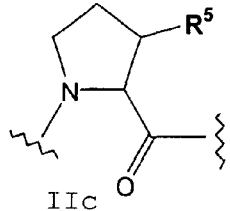

IIa   IIb   IIc

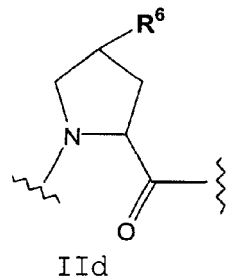 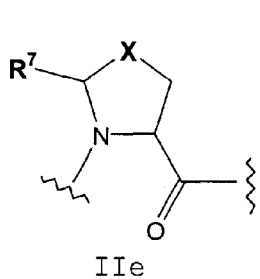 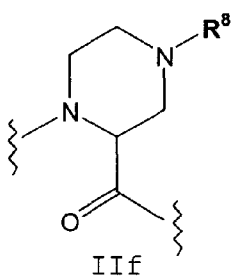

IId   IIe   IIf

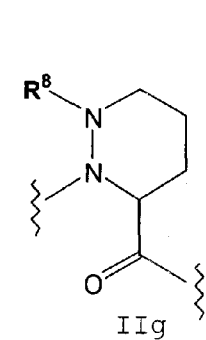 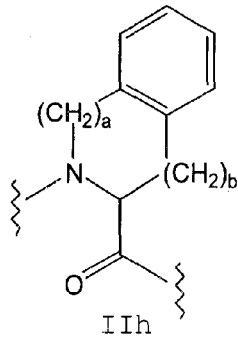 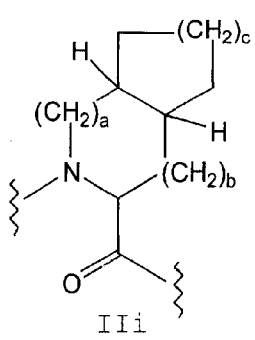

IIg   IIh   IIi

--

UNITED STATES PATENT AND TRADEMARK OFFICE
CERTIFICATE OF CORRECTION

PATENT NO. : 6,515,173 B1
DATED : February 4, 2003
INVENTOR(S) : Robert J. Ternansky et al.

It is certified that error appears in the above-identified patent and that said Letters Patent is hereby corrected as shown below:

Column 36,
Line 50, "$R^3$ is lower alkyl, cycloalkyl, phenyl, $(CH_2)_nNH_2$," should read
-- $R^3$ is lower alkyl, cycloalkyl, phenyl, substituted phenyl, $(CH_2)_nNH_2$, --.

Column 38,
Line 40, "isopropyl, isobutyl, cyclohenxylmethyl," should read -- isopropyl, isobutyl, cyclohexylmethyl, --
Line 47, "and B is $CH^2O(2,3,5,6$-tetrafluorophenyl)." should read -- and B is $CH_2O(2,3,5,6$-tetrafluorophenyl). --

Signed and Sealed this

Twenty-ninth Day of July, 2003

JAMES E. ROGAN
*Director of the United States Patent and Trademark Office*